United States Patent [19]

Bean et al.

[11] 4,061,543

[45] Dec. 6, 1977

[54] BIOASSAY FOR DRUGS AND ANTIBIOTICS

[75] Inventors: Charles P. Bean, Schenectady, N.Y.; Roy J. King, Jr., San Mateo, Calif.; Egidijus E. Uzgiris, Schenectady, N.Y.

[73] Assignee: General Electric Company, Schenectady, N.Y.

[21] Appl. No.: 668,606

[22] Filed: Mar. 19, 1976

[51] Int. Cl.² .............................................. C12K 1/00
[52] U.S. Cl. ........................... 195/103.5 K; 324/71 R
[58] Field of Search ................. 195/103.5 K, 103.5 M; 324/71 R

[56] References Cited

U.S. PATENT DOCUMENTS

| | | | |
|---|---|---|---|
| 3,708,402 | 1/1973 | Bean | 204/199 |
| 3,730,842 | 5/1973 | Wyatt et al. | 195/103.5 K |
| 3,870,612 | 3/1975 | Flygare et al. | 204/180 |
| 3,928,140 | 12/1975 | Wyatt et al. | 195/103.5 K |

OTHER PUBLICATIONS

Optics Communications, vol. 6, pp. 55–57, Sept. 1972.
Immunochemistry, vol. 12, pp. 349–351, Apr. 1975.
Biophysical Journal, vol. 16, Feb. 1976, No. 21, Pt. 2, p. 23a.

*Primary Examiner*—Alvin E. Tanenholtz
*Attorney, Agent, or Firm*—Marvin Snyder; Joseph T. Cohen; Jerome C. Squillaro

[57] ABSTRACT

Effectiveness on cellular processes of a drug or antibiotic introduced into isotonic sucrose solution of 0.005 Normal sodium chloride containing physiological cells in suspension is determined by irradiating the solution, situated in an electric field, with a laser beam and measuring frequency difference between incident light and light scattered by cell motion in the electric field.

6 Claims, 4 Drawing Figures

BIOASSAY FOR DRUGS AND ANTIBIOTICS

This invention relates to a method of determining effectiveness of drugs or antibiotics, and more particularly to a bioassay based on electrokinetic measurements of biological cell mobility as cellular processes are affected by drugs or antibiotics.

No relation between physiological processes and cell mobility values has hitherto been demonstrated. This stems, in part, from a long tradition of performing cell measurements in physiological saline conditions. Yet we have calculated that in more dilute salt concentrations there can be significant changes in cell mobility (approximately 10%) as active membrane transport processes are altered. The present invention concerns a method of carrying out measurements suggested by our calculations. These measurements roughly accord with our expectations and, although they cannot be said to establish uniquely our concepts of the origin of the observed effects, may nevertheless form a basis for a new probe of cellular processes.

Elements essential for carrying out the invention described herein include a sensitive electrokinetic measurement which can provide a quick mobility profile of cell populations, and appropriate solution conditions which will not mask mobility changes associated with cellular physiological processes. Laser scattering techniques are well-suited to the former requirement, and we have found that isotonic sucrose solutions of 0.005 Normal sodium chloride work especially well to reveal the effects of drugs and thereby fulfill the latter requirement.

The measurements necessary to practice the invention can be observed in situ. The antibiotics or drugs to be tested may be added directly to the cell suspension in a light-scattering cuvette and the mobility measurement can be performed in a matter of minutes. In contrast, bioassays for antibiotics or drugs heretofore have required the monitoring of bacterial growth on agar plates or have involved complex biochemical procedures. All such assays have been quite time-consuming.

Accordingly, one object of the invention is to provide a simple, fast assay to test for effectiveness of drugs or antibiotics.

Another object is to provide a method for quickly obtaining a mobility profile of biological cell populations.

Another object is to provide a bioassay for antibiotics or drugs which obviates any need to monitor bacterial growth on agar plates.

Briefly, in accordance with a preferred embodiment of the invention, a method of performing a bioassay to determine effectiveness of medicinal substances upon biological cell mobility comprises suspending cells to be monitored in isotonic sucrose solutions in the range of about 0.02 to 0.001 Normal sodium chloride, of which the higher concentration limit is to avoid losing sensitivity to membrane changes and the lower concentration limit is to maintain good cell stability, and establishing an electric field across at least a portion of the solution. A medicinal substance to be evaluated for efficacy is introduced into the solution over a finite period of time, the solution is irradiated within the electric field with a beam of coherent light, and light scattered by at least some of the cells suspended in the solution is detected. In one embodiment of the invention, frequency difference between the incident beam of coherent light and the light scattered by cells suspended in the solution is measured as a function of medicinal substance applied to indicate efficacy. In another embodiment of the invention, a signal corresponding to a predetermined frequency difference between the incident beam of coherent light and the light scattered by cells suspended in the solution is maintained at a maximum by varying the electric field amplitude as the medicinal substance to be evaluated encounters the cells suspended in the solution, and the resulting changes in electric field amplitude required to maintain maximum signal at the predetermined frequency are measured.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings in which:

DESCRIPTION OF TYPICAL EMBODIMENTS

Figure 1:
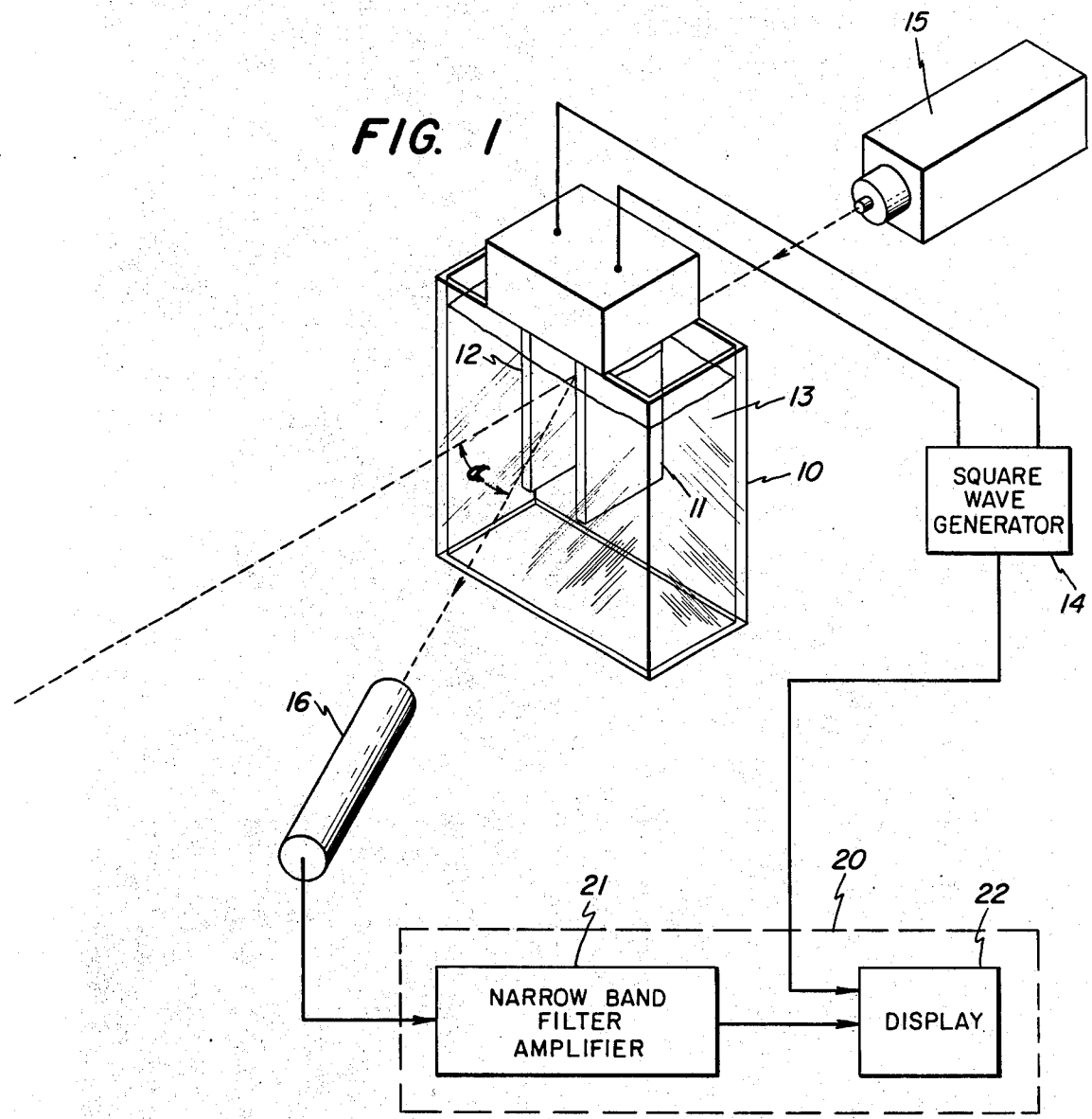
FIG. 1 is a schematic diagram of apparatus employed to practice a first embodiment of the invention.

In FIG. 1, a clear optical cuvette 10 is fitted with internally-located electrodes 11 and 12 to provide means for introducing an electric field therein. The electrodes are preferably of rectangular shape and have mutually parallel facing surfaces defining an interelectrode gap not exceeding one millimeter in width. The cuvette is filled with a dilute salt solution 13, typically an isotonic sucrose solution of about .02 to 0.001 Normal sodium chloride, such as 0.005 Normal sodium chloride, in which physiological cells to be monitored are suspended. The solution between electrodes 11 and 12 may thus be subjected to an electric field produced by a controllably-variable amplitude, low frequency square wave generator 14 connected to the electrodes. Although the electric field between electrodes 11 and 12 need only be a D.C. field, the square wave generator changes polarity at a low frequency which, in a manner known in the art, is maintained sufficiently high to avoid mass transfer, electrode bubbling, and electrode polarization.

A laser 15 illuminates the gap between electrodes 11 and 12 with coherent optical energy. A portion of this energy is scattered by the cells suspended in the solution situated in the gap between electrodes 11 and 12 and, because of motion of the biological cells in the electric field, exhibits a Doppler frequency shift. Energy scattered at a predetermined angle α from the incident laser beam is received by optical detector 16 which is preferably a photomultiplier tube but may be any appropriate square law detector.

Detector 16 receives the Doppler-shifted optical energy scattered by the cells suspended in the solution in cuvette 10, and also receives unshifted optical energy scattered by fixed scattering objects in the vicinity, such as a wall of cuvette 10. Since detector 16 receives both Doppler-shifted and unshifted optical energy, and is a square law detector, its output signal is indicative of the heterodyne product of the two frequencies received. The difference, or beat, frequency is supplied by detector 16 to readout apparatus 20 which, as shown in FIG. 1, comprises a narrow band filter amplifier 21 driven by detector 16 and furnishing an output signal to display apparatus 22 such as an X-Y recorder or oscilloscope display. The bandwidth of filter amplifier 21 is sufficiently wide to accommodate, linearly, the predetermined difference frequency produced by detector 16, but sufficiently narrow to attenuate sharply any signal corresponding to frequencies below or above a narrow band centered on the difference frequency. A signal corresponding to the output voltage amplitude of square wave generator 14 is also furnished to display apparatus 22.

If a medicinal substance to be tested, such as a drug or antibiotic, is introduced into the solution contained in cuvette 10 in a continuously-increasing amount, as by use of a micropipette or other suitable means, while the output voltage of square wave generator 14 is continually readjusted to keep the output signal of detector 16 at a maximum, the changes in electric field strength at electrodes 11 and 12, as measured by output voltage amplitude of square wave generator 14, can constitute an indication of effectiveness of the drug or antibiotic.

Figure 2:
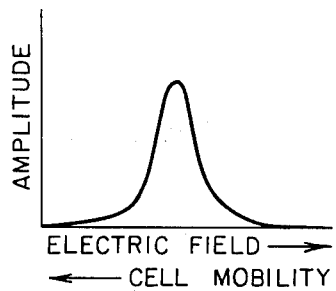
FIG. 2 is a graphical illustration of output signals displayed by the apparatus of FIG. 1.

FIG. 2 is an illustration of a typical graphical display produced by display apparatus 22 of FIG. 1. Amplitude of output signal produced by filter amplifier 21 of FIG. 1, and corresponding to the difference frequency in optical energy impinging on detector 16, is plotted against electric field amplitude across electrodes 11 and 12 of cuvette 10. Any shift along the abscissa, or change in location of any portion of the curve with respect to the electric field axis, constitutes an efficacy indication for the drug or antibiotic. An upward shift along the electric field axis corresponds to a decrease in cell mobility resulting from a reaction between the drug or antibiotic and the cells suspended in the solution.

Figure 3:
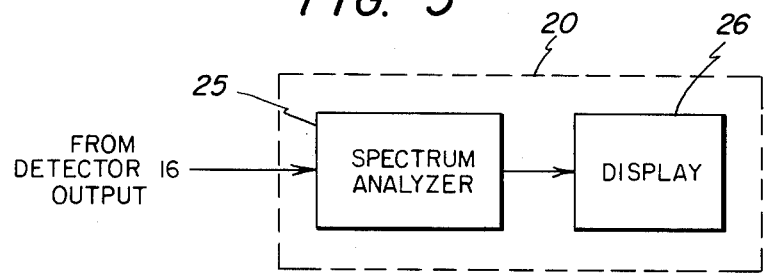
FIG. 3 is a schematic diagram of another type of readout apparatus that may be employed in the optical sensing system of FIG. 1 in order to practice a second embodiment of the invention.

FIG. 3 illustrates an alternate form of readout apparatus 20 that may be employed in the system of FIG. 1. This apparatus comprises a spectrum analyzer 25 receiving the output signal of detector 16, and display apparatus 26 driven by spectrum analyzer 25. In this embodiment, if a drug or antibiotic to be tested is introduced into cuvette 10 slowly, in a continuously-increasing amount, and no change is detected in the difference frequency supplied by detector 16, the ineffectiveness of the drug or antibiotic in changing the transmembrane potential, and hence mobility, of the type of cell suspended in solution 13 is established. The drug or antibiotic concentration needed to change the scattered light frequency by a fixed amount constitutes a measure of effectiveness of the drug or antibiotic.

Figure 4:
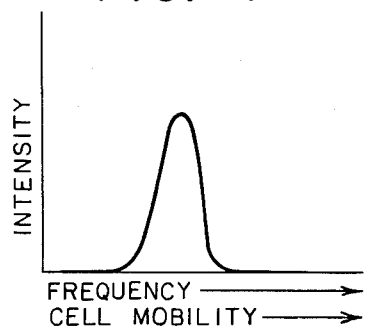
FIG. 4 is a graphical illustration of signals displayed by the readout apparatus of FIG. 3 when connected to the output of the detector in the system of FIG. 1.

FIG. 4 illustrates a typical graphical display of the output signal furnished by detector 16, as presented by display apparatus 26 of FIG. 3 (which may comprise an oscilloscope or X-Y recorder), in the relatively narrow frequency range of interest monitored by spectrum analyzer 25. Intensity of output signal produced by detector 16, as monitored by spectrum analyzer 25, is plotted against the signal frequency. Using this embodiment of the invention, if a drug or antibiotic to be tested is introduced into cuvette 10 slowly, in a continuously-increasing amount, an absence of change in optical difference frequency sensed by detector 16 results in no frequency change in the detector output signal, thus indicating that the drug or antibiotic in question is ineffective in changing the transmembrane potential of the type of cell suspended in solution. Thus a measure of the drug or antibiotic concentration needed to change the scattered light frequency by a fixed amount constitutes a measure of effectiveness of the drug or antibiotic.

When the readout apparatus of FIG. 3 is employed in the system of FIG. 1, any decrease in optical difference frequency sensed by detector 16 indicates a decrease in cell mobility and hence a positive indication of effectiveness of the drug or antibiotic being examined. Specifically, when either human red blood cells or sheep red blood cells were suspended in an isotonic sucrose solution of 0.005 Normal sodium chloride contained in cuvette 10, and minute quantities of either one of the drugs valinomycin and ouabain were introduced in minute quantities to the cell suspensions, each of these drugs being known to interfere with active ionic cell membrane transport, a 10-14% reduction in cell mobility was noted. On the other hand, for similar concentration of each of these drugs on glutaraldehyde fixed cells (i.e., fixed dead cells) no mobility changes were observed. Consequently a theoretical and experimental basis for a new probe of cellular processes has been established.

The foregoing describes a simple and fast assay to test for effectiveness of drugs or antibiotics. The method set forth permits a mobility profile of cell populations to be quickly obtained. The invention constitutes a bioassay for antibiotics or drugs which obviates any need to monitor bacterial growth on agar plates.

While only certain preferred features of the invention have been shown by way of illustration, many modifications and changes will occur to those skilled in the art. It is, therefore, to be understood that the appended claims are intended to cover all such modifications and changes as fall within the true spirit of the invention.

We claim:

1. A method of performing a bioassay to test for effectiveness of medicinal substances upon cell mobility comprising:
    suspending biological cells to be monitored in isotonic sucrose solution substantially in the range of .02 to .001 Normal sodium chloride;
    establishing an electric field across at least a portion of said solution;
    introducing into said solution over a finite period of time a medicinal substance to be examined for efficacy;
    irradiating said solution within said electric field with a beam of coherent light;
    detecting light scattered by at least some of said cells suspended in said solution;
    varying amplitude of said electric field as said medicinal substance to be evaluated encounters said cells suspended in said solution so as to maintain at maximum a signal corresponding to a predetermined frequency difference between the incident beam of coherent light and said light scattered by at least some of said cells suspended in said solution; and
    measuring the resulting changes in electric field amplitude required to maintain said signal at maximum.

2. The method of claim 1 wherein said isotonic sucrose solution contains 0.005 Normal sodium chloride.

3. The method of claim 1 including the step of detecting light scattered by a fixed scattering object in the vicinity of said solution.

4. The method of claim 1 including the step of displaying a plot of amplitude of said signal corresponding to said predetermined frequency difference versus amplitude of said electric field.

5. The method of claim 3 wherein the step of maintaining at maximum a signal corresponding to a predetermined frequency difference between the incident beam of coherent light and said light scattered by at least some of said cells suspended in said solution comprises heterodyning said light scattered by said fixed scattering object and said light scattered by at least some of said cells suspended in said solution to produce an output signal, and filtering said output signal through a narrow band filter passing only signals corresponding to a narrow band of frequencies below and above said predetermined frequency.

6. The method of claim 5 including the step of displaying a plot of amplitude of said output signal supplied by said narrow band filter versus amplitude of said electric field.

* * * * *